(12) United States Patent
Copf

(10) Patent No.: US 6,221,110 B1
(45) Date of Patent: Apr. 24, 2001

(54) SET OF PROSTHESES OF DIFFERENT SIZES

(76) Inventor: Franz Copf, Marienstrasse 12, D-70178 Stuttgart (DE)

( * ) Notice: Subject to any disclaimer, the term of this patent is extended or adjusted under 35 U.S.C. 154(b) by 0 days.

(21) Appl. No.: 09/154,547

(22) Filed: Sep. 16, 1998

(30) Foreign Application Priority Data

Sep. 16, 1997 (DE) ............................................. 197 40 755

(51) Int. Cl.⁷ .................................. A61F 2/32; A61F 2/28
(52) U.S. Cl. .................................................. 623/22; 623/16
(58) Field of Search .............................. 623/16, 18, 20, 623/22, 23

(56) References Cited

U.S. PATENT DOCUMENTS

| | | | | |
|---|---|---|---|---|
| 3,938,198 | * | 2/1976 | Kahn et al. | 623/22 |
| 4,064,567 | * | 12/1977 | Burstein et al. | 430/280.1 |
| 4,068,324 | * | 1/1978 | Townley et al. | 623/23 |
| 4,435,854 | * | 3/1984 | Keller | 623/23 |
| 4,570,271 | * | 2/1986 | Sump | 623/18 |
| 4,728,335 | * | 3/1988 | Jurgutis | 623/23 |
| 5,180,395 | * | 1/1993 | Klaue | 623/23 |
| 5,387,243 | * | 2/1995 | Devanathan | 623/23 |
| 5,507,814 | * | 4/1996 | Gilbert et al. | 623/16 |
| 5,571,185 | * | 11/1996 | Schug | 623/16 |
| 5,766,261 | * | 6/1998 | Neal et al. | 623/16 |
| 5,807,407 | * | 9/1998 | England et al. | 623/16 |

FOREIGN PATENT DOCUMENTS

| | | | | |
|---|---|---|---|---|
| 230006 | * | 7/1987 | (EP) | 623/23 |
| 1627171 | * | 2/1991 | (SU) | 623/23 |

* cited by examiner

Primary Examiner—Paul J. Hirsch
Assistant Examiner—Michael B Priddy

(57) ABSTRACT

A set of prostheses of different sizes comprises in each case a pair of prostheses (10, 10*), which apart from the clear external contour of their anchoring sections (20, 20*) have the same geometry. The anchoring section (20) of a first prosthesis (10) of the pair is constructed as an anchoring section with a cage structure which can be implanted in a cement-free manner, whilst the anchoring section (20*) of the second prosthesis of the pair is constructed as an anchoring section with smooth boundary surfaces which is to be cemented in place. The clear external surface of the anchoring section (20) of the prosthesis (10) which is to be implanted in a cement-free manner lies at a substantially constant distance beyond the clear external surface of the anchoring section (20*) of the prosthesis (10*) which is to be cemented in place. In this manner, the surgeon can still decide, after preparing the bone end, whether he prefers a cemented prosthesis (10*) or a prosthesis (10) which is to be incorporated without cement.

8 Claims, 5 Drawing Sheets

SET OF PROSTHESES OF DIFFERENT SIZES

Figure 1:
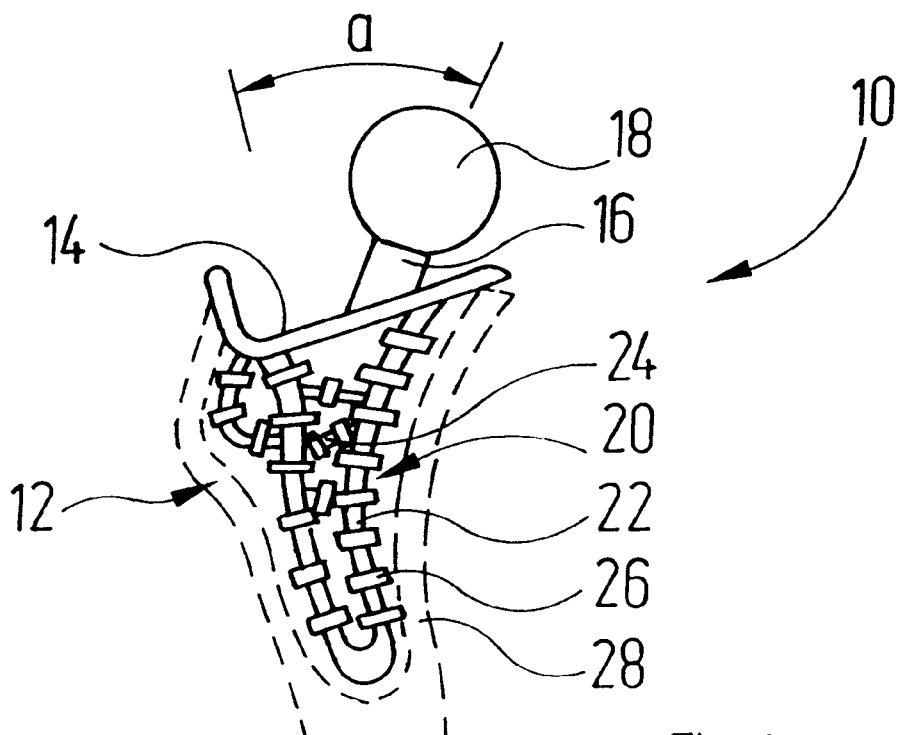

The invention relates to a set of prostheses of different sizes according to the preamble of claim 1.

Sets of prostheses of different sizes are made available by prosthesis manufacturers in order to take into account the different sizes of bones which are found in different patients. The surgeon selects the suitable prosthesis for each individual case from the set which is made available to him.

Furthermore, there are two fundamentally different classes of prosthesis on the market, namely so-called shaft prostheses, which are connected to the wall of a cavity produced in the bone using a cement, and so-called cement-free prostheses, in which the anchoring section introduced into the bone end comprises cavities or openings into which spongiosa can grow during the healing process. Which of these two basic types is used by the surgeon in each individual case needs to be determined prior to the operation.

For some operations, it would be desirable if it were possible to decide between a cemented prosthesis and a prosthesis implanted without cement during the course of the operation depending on the conditions which are encountered.

In order to attain this object, according to the invention a set of prostheses of different sizes is proposed having the features disclosed in claim 1.

According to the invention, the surgeon is therefore provided with a pair of alternative prostheses for use for each standard size, one of which corresponds to the cemented type, the other to the cement-free type. These two prostheses have the same basic geometry, although the exposed external contour of the anchoring section of the cement-free prosthesis lies beyond the clear external contour of the cemented prosthesis; in practice, the distance between these two contours corresponds approximately to the desired thickness of the cement layer between the internal surface of the bone cavity and the external surface of the prosthesis shaft when cementing the cemented prosthesis in place.

For both prostheses, the same resectioning of the corticalis of the end section of the bone which is to be connected to the prosthesis is therefore to be carried out, and the formation of the cavity is also effected in essentially the same manner (with the exception of a possible fine finishing).

For a first provision of a bone with a prosthesis, the cement-free prosthesis is usually preferred, since following the healing process this most closely reproduces the natural structure of a healthy bone. If, after carrying out the appropriate preparation of the bone end, the surgeon ascertains that the cement-free prosthesis is not as suitable after all for the operation which has been performed as the cemented prosthesis, he can easily use a cemented prosthesis instead of the cement-free prosthesis provided.

Advantageous developments of the invention are contained in the subclaims.

The distances given in claim 2 between the clear external contours of the cement-free prosthesis and the cemented prosthesis result in particularly advantageous fitting conditions and particularly advantageous thicknesses of cement layers.

The developments of the invention according to claims 3 to 6 have as their subject matter geometries of the anchoring sections which adapts particularly well to the corticalis of a thigh bone in such a manner that a distance which is substantially constant over the cavity is formed between the clear external contour of the anchoring section of the prosthesis and the internal surface of the cavity defined by the corticalis.

Figure 7:
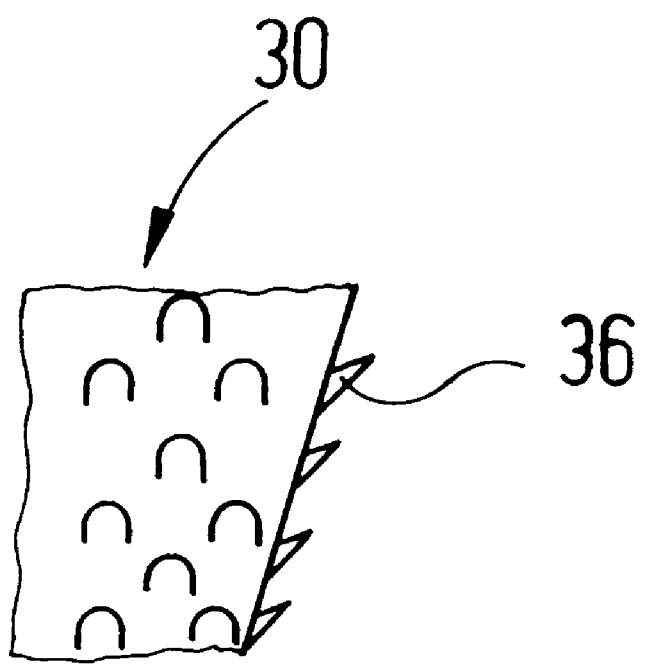
Figure 8:
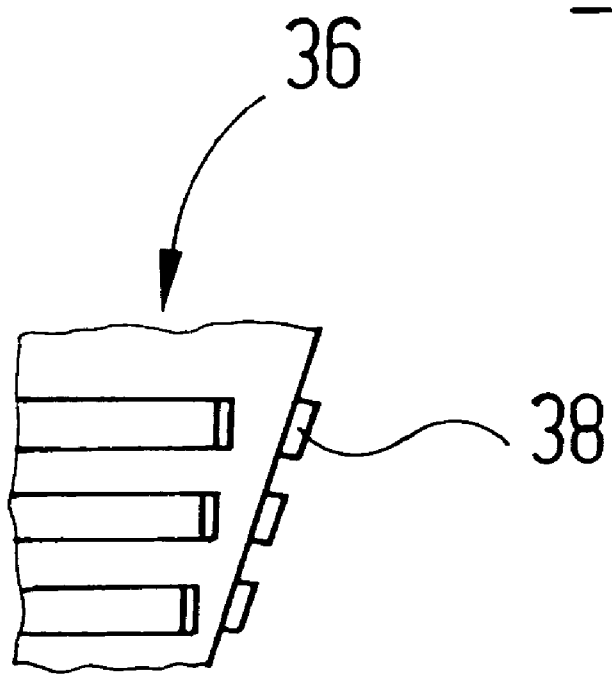

If a tool is used as depicted in FIGS. 7 and 8 for the finishing of the internal surface of the cavity accommodating the anchoring section of the prosthesis which is to be incorporated, then it is ensured on the one hand that an optimal thickness of the cement layer used for the cementing in place is obtained where a cemented prosthesis is used, and on the other hand where a cement-free prosthesis is incorporated that the latter sits with snug friction locking in the cavity.

The above-mentioned advantages are preferably obtained in practice with relationships between the clear external contours of the two prostheses and the tool as depicted in FIGS. 7 and 8.

FIGS. 7 and 8 depict tools which ensure a finishing of the cavity which precisely matches the contour and on the other hand are very simple to manufacture.

Figure 2:
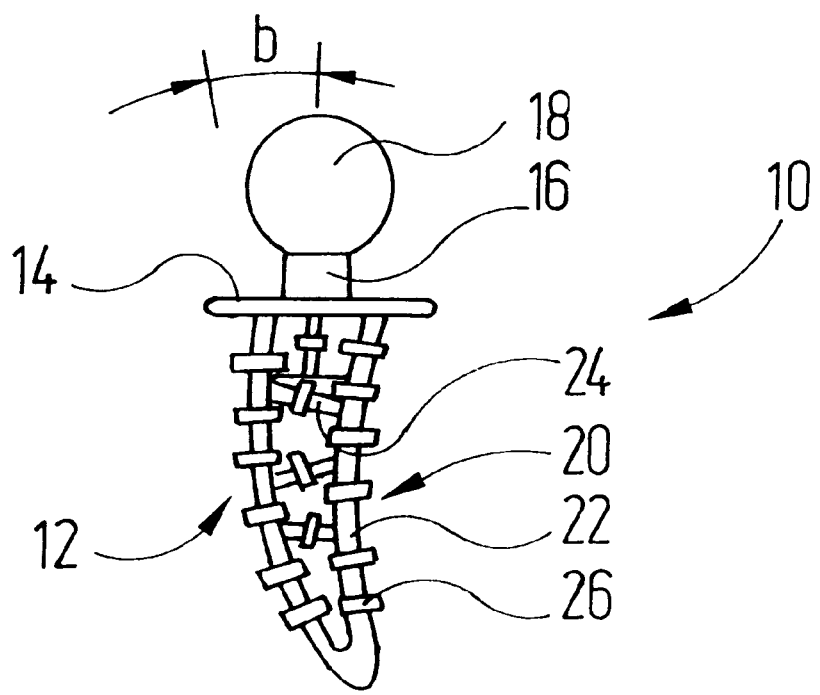
Figure 3:
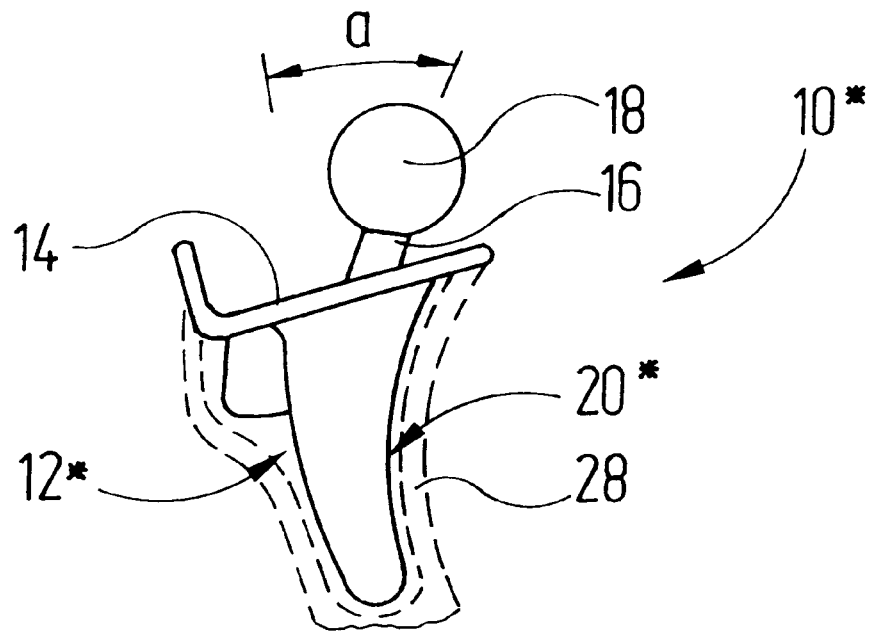
Figure 4:
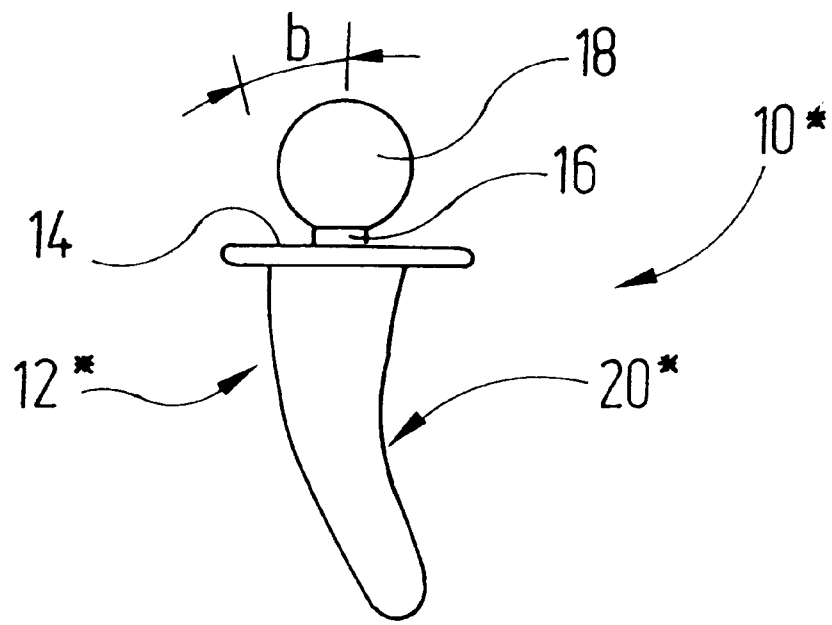
Figure 5:
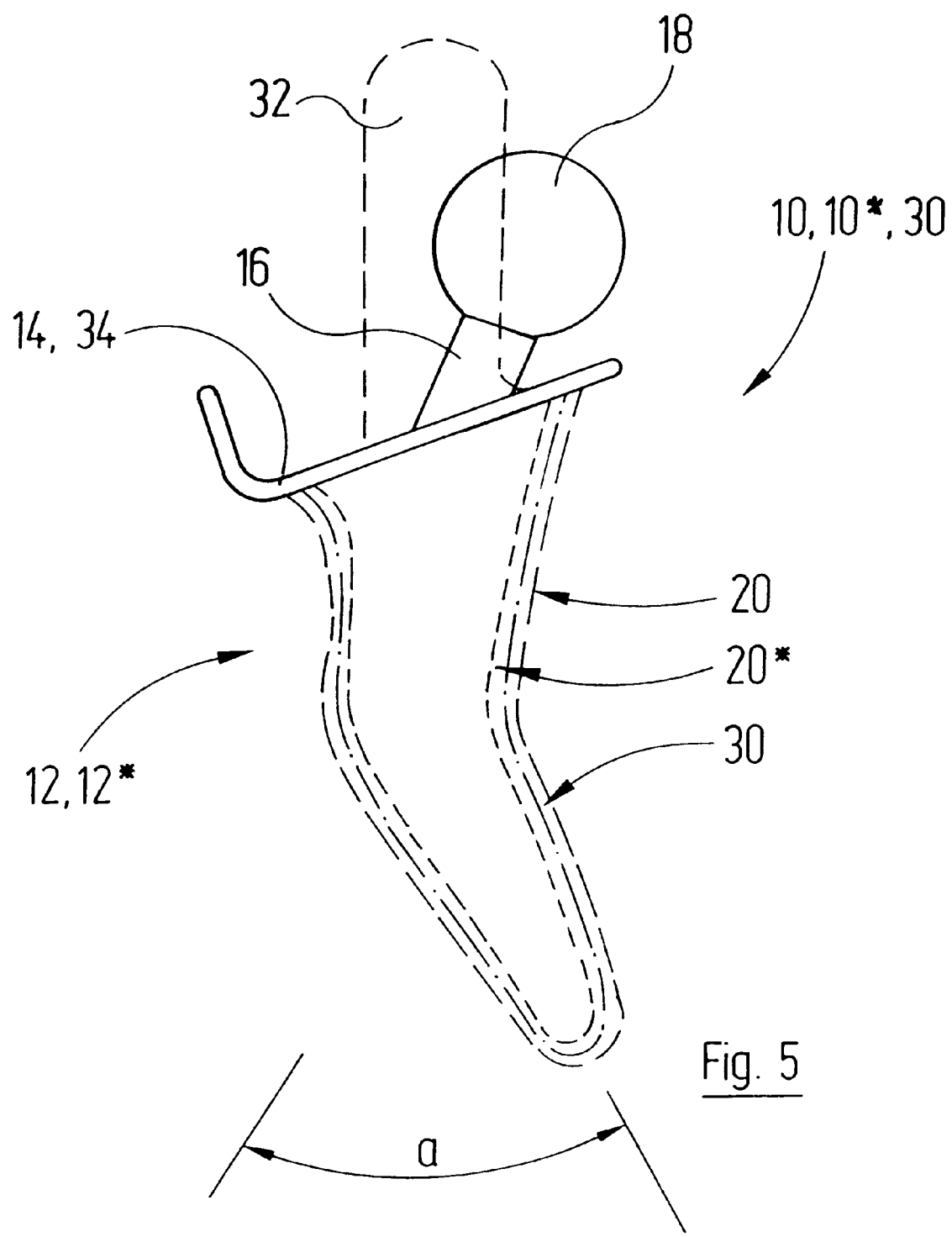
Figure 6:
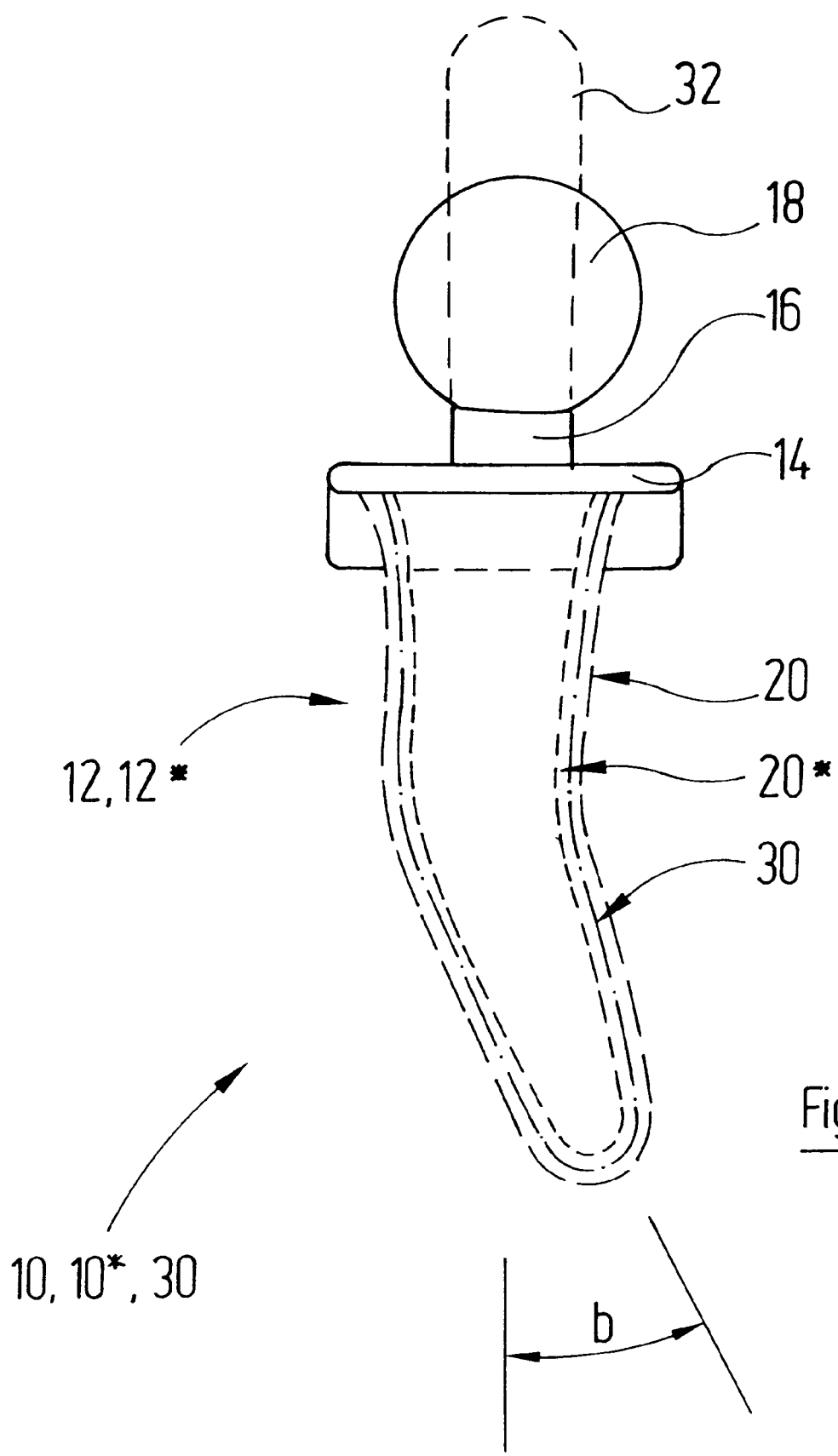

The invention will be explained in further detail in the following with the aid of embodiments with reference to the drawings, in which:

FIG. 1: is a side view of a hip joint prosthesis which is to be implanted in a cement-free manner, viewed in the direction from ventral to dorsal;

FIG. 2 is a side view of the prosthesis according to FIG. 1 in the direction from lateral to medial (from right to left in FIG. 1);

FIGS. 3 and 4: are views corresponding to FIGS. 1 and 2, although showing a prosthesis which is to be cemented in place;

FIGS. 5 and 6; are views corresponding to FIGS. 1 and 2 or 3 and 4, in which the clear external contours of the prosthesis which is to be implanted in a cement-free manner and of the prosthesis which is to be cemented in place are superimposed, and also shown between these two contours is a clear external contour of a tool which is used for finishing the bone cavity receiving the prosthesis;

FIG. 7 is a view of part of the surface of a finishing tool of the rasp type; and FIG. 8 is a view similar to FIG. 6, although showing a finishing tool of the plane type.

In FIG. 1, the reference 10 designates a prosthesis in its entirety, which is incorporated into the thigh of a patient in order to form an artificial hip joint. The prosthesis 10 has a prosthesis element designated in its entirety by the reference 12 with an angled support plate 14. The upper side of the support plate 14 supports a support post 16, which is tilted in the medial direction and to which a condyle 18 is fitted.

The distal boundary surface of the support plate 14 sits on an anchoring section designated in its entirety by the reference 20 and is constructed in the manner of a cage. This comprises main anchoring pillars 22, which essentially form the corners of a pyramid tapering in the distal direction and having a rectangular cross section and are connected by secondary anchoring pillars 24, which in practice can extend in a zig-zag formation between adjacent main anchoring pillars 22.

The main anchoring pillars 22 and the secondary anchoring pillars 24 each support anchoring collars 26, which are spaced apart axially and in practice project 1 to 2 mm beyond the pillar core. The axial dimension of the anchoring collars can be approximately 1 to 2 mm, their axial distance apart approximately 3 to 6 mm.

The prosthesis element is a cast element made of a biocompatible alloy or a forged element which can be subjected to chip-forming finishing on an NC machine.

In the prosthesis shown in FIGS. 3 and 4, which is to be cemented in place, prosthesis elements which have already been explained above in a functionally equivalent form with reference to FIGS. 1 and 2 are again provided with the same reference numerals, to which a "*" is added to distinguish in cases where there are differences. These prosthesis elements are no longer described in detail in the following.

In the prosthesis element according to FIGS. 3 and 4, the space lying between the main anchoring pillars 22 is filled in such a manner that the main anchoring pillars 22 only remain visible as beads 22* on a smooth core. As a modification to the above, the outer curved surfaces of the former main anchoring pillars 22 can also be connected by lateral boundary surfaces lying tangential to the main anchoring pillars 22, so that the latter only remain visible in the form of rounded corners of the substantially rectangular transverse cross section of the anchoring section 20* which tapers towards the distal end of the anchoring section 20*.

As shown in the drawings, the axis of the support post 18 is tilted in the plane formed by the proximal direction and the lateral direction (plane of drawing in FIG. 1) through an angle a relative to the axis of the lower end section of the anchoring section 20 or shaft 20*. In the illustrated embodiment, the angle a measures approximately 35°. The axis of the support post 18 is also tilted in the plane prescribed by the proximal direction and the dorsal direction (plane of drawing in FIG. 2) relative to the lower end section of the anchoring section 20 or shaft 20* through an angle b. In this illustrated embodiment, this measures approximately 15°.

As is already clear from the comparison of FIGS. 1 to 4, the prosthesis types shown therein have a partially identical (upper prosthesis section) and partially geometrically very similar (anchoring section) clear external contour.

As shown in further detail in FIGS. 5 and 6, the external contours of the anchoring sections 20, 20* of the prosthesis 10 which is to be implanted in a cement-free manner and the cemented prosthesis 10* extend at a short, substantially constant distance d parallel to one another. In practice, this distance measures approximately 1 to 2 mm, preferably approximately 1.5 mm. Otherwise, the two prosthesis types have the same geometry, i.e. their support plates 14, their support posts 16 and also the condyles 18 supported by the support posts are identical.

The implantation preparations for the two prosthesis types are identical. The femur, into whose upper end the prosthesis is to be inserted, is resectioned in such a manner that the minor trochanter with the worn condyle is completely removed, whilst a part of the greater trochanter remains. The resectioning line corresponds to the contour of the support plate 14.

The spongiosa is removed from the resectioned bone end by means of a spoon or the like, so that it roughly corresponds to the geometry of an anchoring section 20, but is undersized.

This roughly prepared cavity is subjected to a chip-forming finishing using a finishing tool 30, whose clear external contour is indicated by dot-dash lines in FIGS. 5 and 6. Accordingly, in the embodiment in question the clear external contour of the finishing tool lies without exception approximately in the centre between the two anchoring sections 20 of the prosthesis which is to be implanted in a cement-free manner and the prosthesis which is to be implanted using cement. The distance between the clear external contour of the finishing tool 30 and the clear external contour of the cemented prosthesis generally corresponds to the thickness of the cement layer which is subsequently desired (preferably approximately 1.5 mm), whilst the distance of the clear external contour of the finishing tool 30 from the clear external contour of the prosthesis which is to be implanted without cement corresponds to the thickness of the press-fit of the anchoring section 20 in the corticalis of the femur and preferably measures approximately 0.5 mm.

In FIGS. 5 and 6, a handle of the finishing tool 30 is indicated by the reference 32, and the reference 34 designates a form-locking plate, which is identical in shape to the support plate 14 and is used to position the finishing tool on the resectioning line of the femur.

The finishing tool 30 can be manufactured according to FIG. 7 from a blank, whose external contour corresponds to the clear external contour of the cemented prosthesis and from which individual outwardly projecting rasp teeth are formed by cutting, the tips of said rasp teeth defining the clear external contour of the finishing tool 30.

According to FIG. 8, the finishing tool 30 can also be manufactured from a hollow blank (which is itself manufactured, for example, by deep drawing from sheet metal), from which, by producing incisions and bending the material regions adjacent the incisions, planing blades 38 are then pressed, whose cutting edges define the clear external contour of the finishing tool 30.

What is claimed is:

1. A set of prostheses (10) of different sizes, each prosthesis comprising a support plate (14), to which a condyle joint element (18) is fitted, and an anchoring section (20), which can be introduced into a cavity of a bone (28), wherein the set comprises at least one pair of alternatively useable prostheses (10, 10*), wherein said anchoring section (20) of a first prostheses (10) is to be implanted in a cement-free manner and is more particularly constructed as a cage, and wherein said anchoring section (20*) of a second prosthesis (10*) is constructed as a solid shaft, a clear external contour of the first prosthesis (10) lying at a substantially constant distance beyond and parallel to a clear external contour of the second prosthesis (10*).

2. A prosthesis set as claimed in claim 1, wherein the distance between said clear external contours of the first prosthesis (10) and second prosthesis (10*) measures 1 to 3 mm.

3. A prosthesis set as claimed in claim 1, wherein the transverse cross section of a clear external contour of the anchoring sections (20, 20*) has a substantially rectangular cross section.

4. A prosthesis set as claimed in claim 1, wherein the cross section of the anchoring sections (20, 20*) decreases towards the distal end of the anchoring sections.

5. A prosthesis set as claimed in claim 1, wherein the anchoring sections (20, 20*) each comprise at least one lower section twisted about its longitudinal axis.

6. A prosthesis set as claimed in claim 1, in which the anchoring sections (20, 20*) each comprise a main surface area, which is essentially prescribed by a proximal direction and a distal direction, wherein the anchoring sections (20, 20*) each comprise a proximal lower section and a distal lower section, which in turn comprise lower main surface areas, and the lower main surface areas of the lower sections of the anchoring sections are each tilted relative to one another in such a manner that a bending line extending in the lateral direction is formed between the said lower sections.

7. A prosthesis set as claimed in claim 2, wherein the distance measures approximately 1.5 to 2 mm.

8. A prosthesis set as claimed in claim 3, wherein the rectangular cross section has rounded corners.

* * * * *